United States Patent [19]

Chakraborty et al.

[11] Patent Number: 4,725,619

[45] Date of Patent: Feb. 16, 1988

[54] ARYL AND HETEROARYL ETHERS AS AGENTS FOR THE TREATMENT OF HYPERSENSITIVE AILMENTS

[75] Inventors: Utpal R. Chakraborty, Orangeburg; Raymond D. Youssefyeh, Tarrytown, both of N.Y.

[73] Assignee: USV Pharmaceutical Corporation, Fort Washington, Pa.

[21] Appl. No.: 877,568

[22] Filed: Jun. 23, 1986

Related U.S. Application Data

[62] Division of Ser. No. 723,781, Apr. 16, 1985, Pat. No. 4,631,287.

[51] Int. Cl.$^4$ .................... A61K 31/38; A61K 31/385
[52] U.S. Cl. ........................................ 514/442; 514/443
[58] Field of Search ................................ 514/442, 443

[56] References Cited

PUBLICATIONS

Chem. Abst., vol. 89-146689(r) (1978).
Chem. Abst., vol. 94-192061(f) (1981).

*Primary Examiner*—Stanley J. Friedman

[57] ABSTRACT

The present invention is concerned with the therapeutic composition comprising as an active ingredient a compound of the formula:

$$(R_1)(R_2) Ar-Z-M-Ar_1(R_3)(R_4) \qquad I$$

and salts thereof; wherein

Ar and $Ar_1$ are independently phenyl, naphthyl or a nitrogen, oxygen, or sulfur heterocyclic ring;

Z is an alkylene chain containing from 1 to 5 carbon atoms in the principal chain and up to a total of 10 carbon atoms;

M is oxygen, sulfur, or $NR_5$;

$R_1$, $R_2$, $R_3$ and $R_4$ are each independently H, lower alkyl, lower alkoxy, hydroxy, halo, trihalomethyl, hydroxy lower alkyl, carboxy, formyl, aryl, aryloxy, benzyloxy, lower alkanoyl, carboxy lower alkoxy, nitro, amino, lower alkylamino, dilower alkylamino, cyano, lower alkanoyloxy, carbamoyl, lower alkoxyalkoxy, carbo-lower-alkoxy-alkoxy, or tetrahydropyranylmethyl; and $R_5$ is hydrogen or lower alkyl.

6 Claims, No Drawings

ARYL AND HETEROARYL ETHERS AS AGENTS FOR THE TREATMENT OF HYPERSENSITIVE AILMENTS

This application is a division of copending application Ser. No. 723,781 filed Apr. 16, 1985, U.S. Pat. No. 4,631,287.

This invention relates to the use of certain chemical compounds possessing valuable pharmaceutical activity, particularly as lipoxygenase inhibitors possessing anti-inflammatory and anti-allergic properties U.S. Pat. Nos. 4,327,102 and 4,394,509 and U.K. Patent Application Ser. No. 2,069,492 describe sulfoxides of the formula:

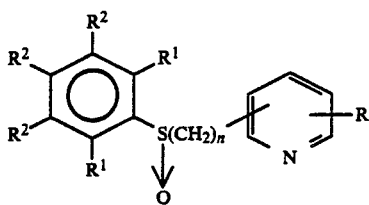

in which R is hydrogen or a hydrocarbon radical, $R^1$ is H or F, $R^2$ is H, F, Cl or $CF_3$, and n is 1 or 2, as anti-ulcer and/or anti-secretory compounds, as well as the corresponding thioether compounds which are prepared by oxidation of the thioether sulfur to the sulfone. The thioethers of the said structure are also described in U.S. Pat. Nos. 4,415,579, 4,394,509 and 4,337,259 as anti-ulcer compounds.

I. *Eur. J. Med. Chem.—Chem. Ther-* 1983-18 (pp. 277-285), described compounds of the following structures as anti-secretory agents:

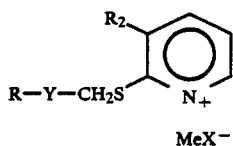
A.

R = various heterocyclics, cyclohexyl, various substituted phenyls;
Y = $CH_2$, S, $(CH_2)_2$, $(CH_2)_3$, CHMe, C=O, C≡C;
$R_2$ = H, CHO, CH$(OEt)_2$

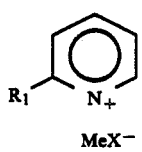
B.

$R_1$ is benzyloxypyridyl quanternary salts, phenylthiomethyl, benzylsulfoxy, benzylthio, etc.

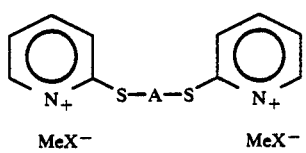
C.

A = alkylene up to $C_5$, and

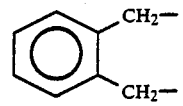

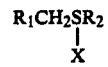
D.

$R_1$ and $R_2$ = various heterocycles, phenyl, substituted phenyl;
X = —, O, $O_2$

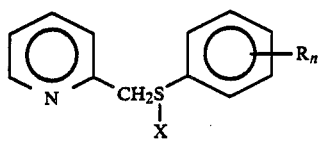
E.

X = — or O;
$R_n$ = H, halogen, or methoxy.

The *Journal of the Pharmaceutical Society of Japan*, 71, 1275-1277 (1951) describes the synthesis of 2-phenoxymethylquinoline, 2-phenoxymethylquinoline-4-carboxylic acid and 3-phenoxy-4-quinoline carboxylic acid from the condensation of isatin and phenoxyacetone under Pfitzinger reaction conditions. No therapeutic properties of these compounds were suggested or disclosed by this article.

Fischer, et al. measure the dissociation constant of various α-substituted -2-picolinium ions and α-substituted-3-picolinium ions in water in the *Canadian Journal of Chemistry*, 56, 3059-3067 and 3068-3071 (1978), respectively. The phenyl substituted 2- and 3-picolinium ions were included in their study. Again, there was no suggestion or teaching regarding the therapeutic efficacy of these compounds.

The *Journal of Medicinal Chemistry*, 26, 218-222, (1983)described 2-[(phenylthio)methyl]pyridines and oxides thereof of the following structures as potential antiarthritic agents:

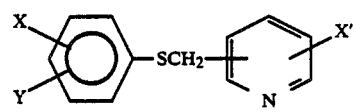
A.

wherein
X is hydrogen, bromo, chloro, fluoro, nitro, t-butyl, methyl, methoxy, amino, acetoamido, hydroxy, trifluoromethyl;
Y is hydrogen, chloro, and t-butyl;
X' is phenyl, chloro, methyl, methoxy, hydroxy, and methylthiophenyl.

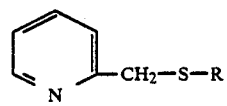
B.

wherein $$R = \text{cyclohexyl}, \text{pyrimidinyl}, \text{pyridyl},$$

$$\text{benzothiazolyl}, \text{benzoxazolyl}, \text{or benzisoxazolyl-carbonyl}$$

*Roreniki, Chem.*, 31, 543–51 (1957), teaches the preparation of 2—$C_6H_4NCH_2SPh$. No therapeutic properties of the compounds were disclosed.

Diaryl ethers are also known in the prior art.

Boyer and Wolford in *J.A.C.S.*, 80, 2741–2743 (1958), describe the synthesis of 2-pyridylmethyl ethers from the reaction of pyridothiazole and phenol. *Pharm. Bull,* 4, 211–216 (1956) decribes the synthesis of picolyl ethers of the formula 4—$PyCH_2OR$, wherein R is lower alkyl, phenyl or benzyl. Neither reference discloses any therapeutic use for these compounds.

The *Journal of Chemical Society, Perkin, I,* 418–425 (1979) describes the synthesis of the compounds possessing the following formula:

$$Ar-CH_2-X-Ar_1$$

wherein
Ar=Ph, p—$MeC_6H_4$, p—$ClC_6H_4$, pyridine or napthalene,
X=O, $CH_2$, S, or $SO_2$
$Ar_1$=pyridine, 4-phenylpyridine, or phenyl.

No physiological application or therapeutic use was disclosed or suggested by this reference.

Thus, the therapeutic activity of these compounds as an anti-inflammatory or as an anti-allergic agent was not recognized or suggested by any of these references mentioned hereinabove.

SUMMARY OF THE INVENTION

The present invention is concerned with the therapeutic composition comprising as an active ingredient a compound of the formula:

$$(R_1)(R_2) Ar-Z-M-Ar_1(R_3)(R_4) \quad\quad I$$

and salts thereof; wherein
Ar and $Ar_1$ are independently phenyl, naphthyl or a nitrogen, oxygen, or sulfur heterocyclic ring;
Z is an alkylene chain containing from 1 to 5 carbon atoms in the principal chain and up to a total of 10 carbon atoms;
M is oxygen, sulfur, or $NR_5$;
$R_1$, $R_2$, $R_3$ and $R_4$ are each independently H, lower alkyl, lower alkoxy, hydroxy, halo, trihalomethyl, hydroxy lower alkyl, carboxy, formyl, aryl, aryloxy, benxzyloxy, lover alkanoyl, carboxy lower alkoxy; nitro, amino, lower alkylamino, dilower alkylamino, cyano, lower alkanoyloxy, carbamoyl, lower alkoxy-alkoxy, crabo-lower-alkoxy-lower-alkoxy or tetrahydropyranylmethyl; and
$R_5$ is hydrogen or lower alkyl.

In addition, the present invention relates to the method of using these compounds a lipoxygenase inhibitors possessing anti-inflammmatory and anti-allergic responses.

The heterocyclic rings exemplary of Ar and $Ar_1$ contain at least one oxygen, sulfur or nitrogen and include the so-called benzoheterocyclic rings. Exemplary heterocyclics include furan, thiophene, pyrrole, pyridine, thiazole, piperazine, oxazole, benzofuran, quinoline, isoquinoline, indole, benzothiophene, benzoxazole, and similar heterocyclic rings as well as the N-oxides of the nitrogen-heterocyclics. The preferred heterocyclic is quinoline.

The alkyl groups, either alone or within the various substituents, defined hereinbefore, are preferably lower alkyl, which may be straight or branched chain and include methyl, ethyl, propyl, isopropyl, butyl, isobutyl, amyl, hexyl and the like.

The halo atoms in halo and trihalomethyl are Cl, Br, I and preferably F. The aryl groups are preferably phenyl.

The preferred compounds are those in which the alkylene chain represented by Z contains from 1-3 carbon atoms and is a normal alkylene chain, most preferably, unsubstituted, Ar is quinoline, $Ar_1$ is phenyl and M is O. Of the substituents on Z, the preferred are lower alkyl, e.g., methyl, ethyl and isopropyl.

Further preference exists for compounds in which Z is methylene and $R_1$, $R_2$ and $R_3$ are H, methoxy, or carboxyisopropoxy or lower alkyl esters thereof and $R_4$ is H, nitro or $OCH_3$.

The present compounds can be prepared by art-recognized procedures from known compounds or readily preparable intermediates. An exemplary general procedure is as follows:

$$(R_1)(R_2)Ar-Z-L + HM-Ar_1(R_3)(R_4) \longrightarrow I$$

$$\quad\quad II \quad\quad\quad\quad\quad\quad III$$

wherein $R_1$, $R_2$, Ar, Z, M, $Ar_1$, $R_3$ and $R_4$ are as defined above, and L is a leaving group, such as halo, tosylate, or mesylate. If M is O or S, any base normally employed to deprotonate an alcohol or thiol may be used, such as sodium hydride, sodium hydroxide, triethyl amine, sodium bicarbonate or diisopropyl/ethylamine.

The above bases may also be used when M is an amine. Reaction temperature are in the range of room temperature to reflux and reaction times vary from 2 to 48 hours. The reaction is carried out in a solvent that will dissolve both reactants and is inert to both as well. Solvents include, but are not limited to, diethyl ether, tetrahydrofuran, N,N- dimethyl formamide, dimethyl sulfoxide, dioxane and the like.

As a further variation, the amino derivatives can be prepared by condensation of an aldehyde $$R_1R_2Ar-Z_2-\overset{O}{\overset{\|}{C}}-H + R_5-\overset{H}{\overset{|}{N}}-Ar_1(R_3)(R_4) \longrightarrow I$$

$$\quad IV \quad\quad\quad\quad\quad\quad V$$

(IV) with a primary amine (V) to form the corresponding imine and the imine is reduced to give a compound of Formula I wherein M is nitrogen and $R_5$ is hydrogen. This product can be alkylated with alkylating agents known in the art, such as alkyl iodides, to form compounds of Formula I wherein M is nitrogen and $R_5$ is lower alkyl. In this process, $R_1$,$R_2$, $R_3$, $R_4$, $R_5$, Ar and $Ar_1$ are as defined hereinabove and $Z_2$ is an alkylene chain containing 0 to 4 carbon atoms.

The aforementioned condensation reaction to form imines with subsequent hydrogenation can be conveniently carried out in a single reaction zone by the expendiency of mixing the aldehyde (IV) with the amine (V) under hydrogenation conditions. For practical purposes, the aforesaid reactants can be hydrogenated over noble metal catalysts such as palladium over platinum, rhodium, ruthenium, and the like, and the two stages occur under such conditions to produce the desired end products. Alternatively, the imine can be reduced with Lewis acids, such as NaBH$_3$CN, sodium borohydride and the like under the above conditions.

As in any organic reaction, solvents can be employed, such as methanol, methylene chloride, chloroform, tetrahydrofuran, dioxane, diethyl ether, ethanol and the like. The reaction is normally effected at or near room temperature, although temperatures from 0° C. up to the reflux temperature of the rection mixture can be employed.

The present compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, sulfuric, nitric, benzenesulfonic, toluenesulfonic, acetic, malic, tartaric and the like which are pharmaceutically acceptable. Basic salts for pharmaceutical use are the Na, K, Ca, and Mg salts.

Various substituents on the present new compounds, e.g., as defined in R, $R_1$, $R_2$, and $R_3$ can be present in the starting compounds, added to any one of the intermediates or added after formation of the final products by the known methods of substitution or conversion reactions. If the substituents themselves are reactive, then the substituents can themselves be protected according to the techniques known in the art. A variety of protecting groups known in the art may be employed. Examples of many of these possible groups may be found in "Protective Groups in Organic Synthesis" by T. W. Green, John Wiley and Sons, 1981. For example, the nitro groups can be added to the aromatic ring by nitration and the nitro group converted to other groups, such as amino by reduction, and halo by diazotization of the amino group and replacement of the diazo group. Alkanoyl groups can be substituted onto the aryl groups by Friedel-Crafts acylation. The acyl groups can then be transformed to the corresponding alkyl groups by various methods, including the Wolff-Kishner reduction and Clemmenson reduction. Amino groups can be alkylated to form mono and dialkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

The compounds of the present invention can be administered to the host in a variety of forms adapted to the chosen route of administration, i.e., orally, intravenously, intramuscularly or subcutaneous, topically or inhalation routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet For oral therapeutic administration, the active compound may be incorporated with excipients and used in the form of ingestible tablets, buccal tablets, troches, capsules, elixirs, suspensions, syrups, wafers, and the like Such compositions and preparations should contain at least 0.1% of active compound. The percentage of the compositions and preparations may, of course, be varied and may conveniently be betweeh about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The following examples further illustrate the invention.

EXAMPLE 1

2-Phenoxymethyl quinoline

A mixture of 2-chloromethyl quinoline (0.05 mol), phenol (0.055 mol), finely powdered potassium carbonate (0.055 mol), cesium carbonate (0.005 mol) and sodium iodide (0.0025 mol) in acetone was refluxed for about 4 hours. The reaction mixture was cooled to room temperature and filtered and the filtrate was concentrated and dissolved in ether. The ether solution was washed thoroughly with 1N NaOH solution, water and brine. After drying the ether solution over anhydrous magnesium sulfate, and filtering off the drying agent, the solvent was evaporated off to leave the crude product which was crystallized from hexane and ether to yield the desired compound as a light yellow solid, m.p. 79.5°–80.5° C.

EXAMPLE 2

2-(p-Nitrophenoxymethyl) quinoline

This compound was prepared in an identical manner as described in Example 1, except p-nitrophenol was substituted for phenol, m.p. 142°–143° C.

EXAMPLE 3

2-(p-Methoxyphenoxymethyl) quinoline

This compound was prepared in an identical manner as described in Example 1, except p-methoxyphenol was substituted for phenol, m.p. 79°–80° C.

In a similar fashion according to the procedures of the preceding examples, the following compounds can be prepared from approproate starting materials:
2-phenoxymethyl pyridine;
2-phenoxymethyl furan;
2-phenoxymethyl oxazole;
1-phenoxymethyl isoquinoline;
2-phenoxymethyl indole;
2-phenoxymethyl benzoxazole;
2-phenoxymethyl thiophene;
2-phenylthiomethyl quinoline;
1-phenylthiomethyl isoquinoline;
2-phenylthiomethyl furan;
2-phenylthiomethyl indole;
2-phenylthiomethyl thiophene;
2-phenylaminomethyl pyridine;
2-phenylaminomethyl quinoline;
1-phenylaminomethyl isoquiholine;
2-phenylaminomethyl indole;
2-phenylaminomethyl thiophene;
3-phenoxymethyl quinoline;
3-phenoxyethyl quinoline;
3-phenoxymethyl isoquinoline;
2-(2-pyridyloxymethyl)quinoline;
1-(2-imidazolyloxyethyl)isoquinoline;
2-(3-pyrrolyloxymethyl)quinoline;
2-(2-indoloxymethyl)quinoline;
2-(2-naphthyloxymethyl)quinoline;
2-(2-naphthyloxymethyl)quinoline;
2-(2-thienyloxymethyl)quinoline;
2-(2-furyloxymethylmethyl)quinoline;
2-(2-(benzyloxyphenyl)quinoline;
α-phenoxymethylnaphthalene;
p-phenylthiomethyltoluene;
α-phenylthioethylnaphthalene;
p-phenylaminomethylphenol;
β-phenylaminopropylnaphthalene)
p-(2-pyridyloxymethyl)anisole;
β-(2-imidazolyloxymethylnapthalene)
2-phenylpropyloxythiophene;
2-benzyloxyfuran;
2-benzyloxypyridine.
4-phenoxymethylquinoline
4-phenoxymethylisoquinoline
8-phenoxyquinoline
8-benzyloxyquinoline
2-(2-quinolylmethoxymethyl)quinoline
2-(2-pyridylmethoxymethyl)quinoline
1-(2-quinolylmethoxymethyl)isoquinoline
2-(3-carboxyphenoxymethyl)quinoline
2-(3-cyanophenoxymethyl)quinoline
2-(4-fluorophenoxymethyl)quinoline
2-(3-trifluoromethylphenoxymethyl)quinoline
2-(4-butoxyphenoxymethyl)quinoline
6-methoxy-2-(4-fluorophenoxymethyl)quinoline
8-methoxy-2-(3-trifluoromethylphenoxymethyl)quinoline
1-(3-butoxyphenoxymethyl)isoquinoline
1-(3-butylphenoxymethyl)isoquinoline
6-propionyloxy-2-(3-carboxyphenoxymethyl)quinoline
8-propionyloxy-2-(3-butoxyphenoxymethyl)quinoline
6-carbethoxyisopropoxy-2-(3-carboxyphenoxymethyl)-quinoline
8-carbethoxyisopropoxy-2-(3-carboxyphenoxymethyl)-quinoline
2-(3-(carbethoxyphenoxy)methyl)quinoline
2-(3-(carboxyphenoxy)methyl)quinoline
2-(3-(cyanophenoxy)methyl)quinoline
1-(3-(trifluoromethylphenoxy)methyl)isoquinoline
1-(3-(fluorophenoxy)methyl)isoquinoline
1-(3-(chlorophenoxy)methyl)quinoline
2-(3-(butoxyphenoxy)methyl)quinoline
2-(m-tolyloxymethyl)quinoline
2-(3-(benzyloxy)methyl)quinoline
2-(4-(phenoxyphenoxy)methyl)quinoline
2-(3,5-dichlorophenoxymethyl)quinoline
2-(3,4-dimethoxyphenoxymethyl)quinoline
2-(4-fluorophenoxymethyl)-6-methoxyquinoline
2-(3-butoxyphenoxymethyl)-6-methoxyquinoline
2-(4-fluorophenoxymethyl)-8-methoxyquinoline 2-(3-carboxyphenoxymethyl)-8-methoxyquinoline
2-(3-carboxyphenoxymethyl)-6-methoxyquinoline
2-(3-trifluoromethylphenoxymethyl)-7-methoxyquinoline
2-(3-chlorophenoxymethyl)-6-methoxyquinoline
8-(3-n-butoxy)benzyloxyquinoline
1-(3-n-butoxyphenoxymethyl)isoquinoline
2-(3-trifluorophenoxy)-6-methoxyquinoline
2-(3-carboxyphenoxy)-7-methoxyquinoline
8-(3-n-butylbenzyloxy)quinoline
1-(3-carboxyphenoxymethyl)isoquinoline
2-(4-(4-tetrahydropyranylmethyl)phenoxymethyl)quinoline The compounds of the present invention have potent activity in regulating lipoxygenase and as such possess therapeutic value in the treatment of inflammatory conditions and allergic responses such as anaphlaxis and asthma.

Lipoxygenases in mammals have been found in the lung, platelets, and white cells. They are enzymes capable of oxidizing arachidonic acid into hydroperoxyeicosatetraenoic acids (HPETEs) and their stable products hydroxyeicosatetraenoic acids (HETEs). Lipoxygenases are classified according to the position in the arachidonic acid which is oxygenated. Platelets metabolize arachidonic acid to 12-HETE, while polymorphonuclear leukocytes contain 5 and 15 lipoxygenases. It is known that 12-HETE and 5, 12-diHETE are chemotactic for human neutrophils and eosinophils, and may augment the inflammation process. 5-HPETE is known to be a precursor of slow-reacting substance of anaphylaxis (SRS-A). The SRS family of molecules, such as leukotrienes C, D, and E have been shown to be potent bronchoconstrictors (see, NATURE 288, 484–486 (1980)).

The following protocol describes an assay to detect inhibitors of the lipoxygenase pathway. Such inhibitors are believed to be capable of modulating the biosynthesis of the leukotrienes, a property believed to be useful in treating asthma and inflammatory disease states.

Protocol for Detecting Inhibitors of the Lipoxygenase Pathway

A suspension of rat neutrophils in buffer is incubated for 3 minutes at 30° C. with ($^{14}$C)-arachidonic acid (AA) and Calcium Ionophore A23187. Citric acid (2M) is used to quench the reaction. Following the addition of a trace amount of ($^3$H)-5-HETE together with an excess of unlabeled 5-HETE to each tube, the mixture is extracted with chloroform/methanol. The organic layer is washed with dilute acid and an aliquot is transferred to glass tubes and dried. The residue is dissolved in a small volume of chloroform and an aliquot is spotted on silica gel TLC sheets, which are developed with an ethyl acetate/isooctane/water/acetic acid solvent system. The 5-HETE spots are visualized with iodine, cut out and placed in scintillation vials for counting. After adjusting for the extraction efficiency, the amount (pmole) of ($^{14}$C)-5-HETE in each of the tubes is quantitated by substracting the net pmoles of 5-HETE in the tubes containing buffer along (blank) from the pmoles of 5HETE in the tubes containing buffer and cells (control). The ability of the test compounds to modulate the activity of this enzyme is determined by a decrease or increase in the net amount of
-5-HETE produced.

2-Phenoxymethyl quinoline and 2-(p-methoxyphenoxymethyl) quinoline on such testing indicated a value of $I_{50}$=0.5 $\mu$M and 0.7 $\mu$M, respectively, illustrating potent inhibiting activity of the present compounds.

Leukotrienes, the products of the 5-lipoxygenase pathway of arachidonic acid metabolism, are potent contractile agents with a variety of smooth muscle preparations. Thus, it has been hypothesized that the leukotrienes contribute significantly to the pathophysiology of asthma. The following protocol describes an in vitro assay used to test compounds which specifically antagonize the actions of leukotrienes.

Protocol for SRS-A (slow reacting substance of anaphylaxis) Antagonists

Peripheral strips of guinea pig lungs are prepared and hung in tissue baths (Metro #ME-5505, 10 ml) according to the published procedure—(Proc. Nat'l Acad. Sci., U.S.A. Volume 77, pp. 4354 – 4358, 1980). The strips are thoroughly rinsed in Assay Buffer and then connected with surgical silk thread to support rods from the tissue baths. The rods are adjusted in the baths and the strips connected to the pressure transducers (Grass FT 103 or Gould UC-3). The tissue baths are aerated with 95% oxygen - 5% carbon dioxide and maintained at 37° C. The assay buffer has been made as follows: for each liter of buffer the following are added to approximately 800 ml of water distilled in glass-6.87 g NaCl, 0.4 g KCl, 2.1 g NaHCO$_3$, 0.14 g NaH$_2$PO$_4$.H$_2$O, 0.21 g MgSO$_4$. 7H$_2$O, and 2.0 g D-glucose. Then a solution of 0.368 g CaCl$_2$.2H$_2$O in 100 ml glass-distilled water is slowly added to the buffer. Sufficient water is added to adjust the volume to one liter, and the solution is aerated with 95% oxygen-5% carbon dioxide. Usually 10 liters of buffer are used for an experiment with 4 tissues.

After the tissues have been repeatedly washed and allowed to equilibrate in the tissue bath, they are challenged with 1 $\mu$M histamine. After maximum contractions habe been obtained, the tissues are washed, and allowed to relax back to baseline tension. This histamine challenge procedure is repeated at least 1 to 2 more times to obtain a repeatable control response. The average response to 1 $\mu$M histamine for each tissue is used to normalize all other challenges.

Responses of each tissue to a pre-determined concentration of leukotriene are then obtained. Usually test compounds are examined initially at 30 $\mu$M on resting tension of the tissues without any added agonist or antagonist to determine if the compound has any possible intrinsic activity. The tissues are washed and the test compound is added again. Leukotriene is added after the desired pre-incubation time. The intrinsic activity of the compounds, and their effect on leukotriene-induced contractions are then recorded.

The concentration required for 50% inhibition of 0.2 nM leukotriene C$_4$-induced contraction of guinea pig peripheral strips for 2-phenoxymethyl quinoline and 2-(p-methoxyphenoxymethyl)quinoline were 0.9 $\mu$M and 0.3 $\mu$, respectively.

Representative compounds of the present invention were also tested in the following in vivo model. Protocol for in vivo Testing of Modulators of SRS-A (slow reacting substances of anaphylaxis).

This test, known as the Bronchial Anaphylaxis in Guinea Pigs with Enhanced Leukotrienes (BAGEL), is based on the procedure published in Agents and Actions, Vol. II, pp. 396-401, 1981, and is performed with guinea pigs actively immunized (14 days) with ovalbumin (2.7 mg/kg, i.p.) and B. pertussis (5 × 10$^9$ organisms)

as an adjuvant. Prior to challenge with antigen (ovalbumin), the animals are anesthetized and prepared for monitoring pulmonary dynamics by whole body plethysmography. They are treated with an $H^1$ antihistamine (methapyrilene, 2mg/kg, i.v.) and cyclooxygenase inhibitor (indomethacin; 20 mg/kg, i.p.) in order to enhance the SRS-A component of anaphylactic bronchoconstriction. Bronchoconstriction is quantified as the maximum increase in airway resistance following antigen challenge. The drug is administered either i.p. 10 minutes before challenge, or i.d. 15 minutes before challenge.

2-Phenoxymethyl quinoline was highly active at 100 mg/kg, i.d.

What is claimed is:

1. A method for the treatment of hypersensitive, inflammatory or allergic conditions in a mammal, comprising the administration to said animal of a therapeutically effective amount of a compound having the following formula:

$$(R_1)(R_2)Ar-Z-M-Ar_1(R_3)(R_4)$$

and salts thereof; wherein
Ar and $Ar_1$ are independently an unsaturated sulfur heterocyclic ring;
Z is an alkylene chain containing from 1 to 5 carbon atoms in the principal chain and up to a total of 10 carbon atoms;
M is oxygen, sulfur or $NR_5$;
$R_1$, $R_2$, $R_3$ and $R_4$ are each independently H, lower alkyl, lower alkoxy, hydroxy, halo, trihalomethyl, hydroxy lower alkyl, carboxy, formyl, aryl, aryloxy, benzxyloxy, carboxy lower alkoxy, nitro, amino, lower alkylamino, dilower alkylamino, cyano, lower alkanoyloxy, carbamoyl, or lower-alkoxy-alkoxy; and
$R_5$ is hydrogen or lower alkyl
in a pharmaceutically acceptable carrier.

2. The method according to claim 1 wherein M is oxygen.

3. The method according to claim 1 wherein Z contains 1 to 2 carbon atoms in the principal chain, $R_1$, $R_2$ and $R_3$ are H, methoxy, or carboxyisopropoxy or lower alkyl esters thereof and $R_4$ is H, nitro or methoxy.

4. A therapeutic composition for the treatment of hypersensitive, inflammatory or allergic conditions comprising as an active ingredient an effective amount of a compound of a formula $$(R_1)(R_2)Ar-M-Ar_1(R_3)(R_4)$$

and salts thereof; wherein
Ar and Arl are independently an unsaturated sulfur heterocyclic ring;
Z is an alkylene chain containing from 1 to 5 carbon atoms in the principal chain and up to a total of 10 carbon atoms;
M is oxygen, sulfur, or $NR_5$;
$R_1$, $R_2$, $R_3$ and $R_4$ are independently H, lower alkyl, lower alkoxy, hydroxy, halo, trihalomethyl, hydroxy-lower alkyl, carboxy, formyl, aryl, aryloxy, benzxyloxy, carboxy lower alkoxy, nitro, amino, lower alkylamino, dilower alkylamino, cyano, lower alkanoyloxy, carbamoyl, or lower alkoxy-alkoxy, and
$R_5$ is hydrogen or lower alkyl in a pharmaceutically acceptable carrier.

5. The therapeutic composition according to claim 1 wherein M is oxygen.

6. The therapeutic composition according to claim 4 wherein Z contains one to two carbon atoms in the principal chain, $R_1$, $R_2$, $R_3$ are each H, methoxy or carboxy isopropoxy or lower alkyl esters thereof and R4 is H, nitro or methoxy.

* * * * *